(12) United States Patent
De Winne

(10) Patent No.: US 9,884,805 B2
(45) Date of Patent: Feb. 6, 2018

(54) METHOD FOR PRODUCING N-ETHYL-DIISOPROPYLAMINE

(71) Applicant: BASF SE, Ludwigshafen (DE)

(72) Inventor: Hendrik De Winne, Mechelen (BE)

(73) Assignee: BASF Antwerpen NV (BE)

( * ) Notice: Subject to any disclaimer, the term of this patent is extended or adjusted under 35 U.S.C. 154(b) by 0 days.

(21) Appl. No.: 15/119,203

(22) PCT Filed: Feb. 6, 2015

(86) PCT No.: PCT/EP2015/052500
§ 371 (c)(1),
(2) Date: Aug. 16, 2016

(87) PCT Pub. No.: WO2015/124442
PCT Pub. Date: Aug. 27, 2015

(65) Prior Publication Data
US 2017/0008831 A1    Jan. 12, 2017

(30) Foreign Application Priority Data

Feb. 18, 2014    (EP) .................................... 14155557

(51) Int. Cl.
| | | |
|---|---|---|
| C07C 209/26 | (2006.01) | |
| B01J 21/04 | (2006.01) | |
| B01J 21/18 | (2006.01) | |
| B01J 23/44 | (2006.01) | |
| B01J 35/12 | (2006.01) | |

(52) U.S. Cl.
CPC .............. *C07C 209/26* (2013.01); *B01J 21/04* (2013.01); *B01J 21/18* (2013.01); *B01J 23/44* (2013.01); *B01J 35/12* (2013.01)

(58) Field of Classification Search
CPC ... B01J 21/04; B01J 21/18; B01J 23/44; B01J 35/12; C07C 209/26
See application file for complete search history.

(56) References Cited

U.S. PATENT DOCUMENTS

| | | | |
|---|---|---|---|
| 2,692,285 A | 10/1954 | Robinson | |
| 2,695,267 A * | 11/1954 | Challis | C07C 29/82 |
| | | | 203/68 |
| 5,530,127 A | 6/1996 | Reif et al. | |
| 6,288,064 B1 | 9/2001 | Watanabe et al. | |
| 8,034,978 B2 | 10/2011 | Eberhardt et al. | |
| 2010/0267948 A1 * | 10/2010 | Eberhardt | C07C 209/26 |
| | | | 544/106 |

FOREIGN PATENT DOCUMENTS

| | | |
|---|---|---|
| EP | 563327 A1 | 10/1993 |
| EP | 696572 A1 | 2/1996 |
| EP | 1020424 A1 | 7/2000 |
| JP | H02180854 A | 7/1990 |
| JP | H1081650 A | 3/1998 |
| JP | 2740828 B2 | 4/1998 |
| JP | 2851274 | 1/1999 |
| WO | WO-9210290 A1 | 6/1992 |
| WO | WO-98/07430 A1 | 2/1998 |
| WO | WO-2007/137990 A1 | 12/2007 |
| WO | WO-2013/075974 A1 | 5/2013 |

OTHER PUBLICATIONS

Bahn et al., "The Catalytic Amination of Alcohols," 2011, 3, 1853-1864.*
Biradar et al., "Silica-Dendrimer Core—Shell Microspheres with Encapsulated Ultrasmall Palladium Nanoparticles: Efficient and Easily Recyclable Heterogeneous Nanocatalysts," Langmuir 2011, 27(23) 14408-14418.*
International Preliminary Examination Report with Applicant response for PCT/EP2015/052500 dated Jan. 29, 2016.
International Search Report for PCT/EP2015/052500 dated May 12, 2015.

* cited by examiner

*Primary Examiner* — Pancham Bakshi
*Assistant Examiner* — Mark Luderer
(74) *Attorney, Agent, or Firm* — Drinker Biddle & Reath LLP

(57) ABSTRACT

A process for preparing N-ethyldiisopropylamine by reacting acetaldehyde with diisopropylamine and hydrogen at elevated temperature and under pressure in the presence of a heterogeneous hydrogenation catalyst, the catalyst being a supported transition metal catalyst comprising Pd and/or Pt as catalytically active metal, wherein the diisopropylamine used has a purity of 58% to 94% by weight and impurities as follows:
3% to 20% by weight of water, 3% to 20% by weight of isopropanol, 0% to 2% by weight of others.

16 Claims, No Drawings

METHOD FOR PRODUCING N-ETHYL-DIISOPROPYLAMINE

CROSS-REFERENCE TO RELATED APPLICATIONS

This application is a national stage application (under 35 U.S.C. § 371) of PCT/EP2015/052500, filed Feb. 6, 2015, which claims benefit of European Application No. 14155557.3, filed Feb. 18, 2014, both applications of which are incorporated herein by reference in their entirety.

The present invention relates to a process for preparing N-ethyldiisopropylamine (EDIIPA, Hünig's base) of the formula

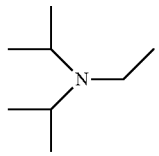

by reacting acetaldehyde with diisopropylamine (DIIPA) and hydrogen at elevated temperature and under pressure in the presence of a hydrogenation catalyst.

BACKGROUND OF THE INVENTION

N-Ethyldiisopropylamine is an important amine which, being a strong base of low nucleophilicity, is used in elimination reactions and finds use as catalyst or auxiliary base in the organic synthesis of, for example, active ingredients (see, for example, WO 98/07430 A).

Chem. Ber. 91, pages 380-392 (1958), describes the synthesis of N-ethyldiisopropylamine by reaction of diisopropylamine with diethyl sulfate. This affords sulfates as unwanted by-products, which subsequently have to be disposed of in a costly and inconvenient manner.

The reaction of diisopropylamine with ethyl iodide for synthesis of N-ethyldiisopropylamine, described in J. Org. Chem. 16, pages 1911-1920, (1951) and U.S. Pat. No. 2,692,285 A, also leads to unwanted salts as by-products.

JP 10081650 A2, granted as JP 2851274 B2 (Koei Chem.), and JP 02180854 A2, granted as JP 2740828 B2 (Koei Chem.), especially describe the preparation of N-ethyldiisopropylamine from acetaldehyde and diisopropylamine or from acetone and ethylamine over Pd/C suspension catalysts in semi-batchwise mode at 20-200° C. and preferably 5-60 atm.

EP 1 020 424 A1 (BASF AG) describes a process for preparing N-ethyldiisopropylamine by reacting acetaldehyde with diisopropylamine and hydrogen at elevated temperature and under pressure in the presence of a hydrogenation catalyst, wherein the catalyst comprises an oxidic support material selected from the group of zirconium dioxide, titanium dioxide, aluminum oxide, silicon dioxide, zinc oxide, magnesium oxide, cerium dioxide, clays and zeolites or mixtures thereof. Preferred catalysts are, for example, $Pd/Al_2O_3$, $Pt/ZrO_2$, $Pd+Ag/SiO_2$, $Ru/Al_2O_3$, $Pd/ZrO_2$.

WO 2007/137990 A1 (BASF AG) teaches processes for preparing an amine by reacting an aldehyde and/or ketone with hydrogen and a nitrogen compound selected from the group consisting of primary and secondary amines in the presence of a heterogeneous catalyst, wherein the reaction is carried out using a suspended catalyst as heterogeneous catalyst and is carried out in the semibatch mode in which the nitrogen compound as one reactant is placed in the reaction vessel and the aldehyde and/or the ketone as the other reactant is added during the course of the reaction and the aldehyde and/or the ketone is added in portions or continuously to the reaction mixture during the course of the reaction as a function of the achieved conversion of the nitrogen compound until a conversion of the nitrogen compound of at least 95% results, and all or part of the catalyst remains in the reaction vessel after the reaction batch and is reused for the next reaction batch.

One particular embodiment is the preparation of Hünig's base by reaction with acetaldehyde with diisopropylamine using a Pd/C suspension catalyst (loc. cit., bottom of page 14).

DETAILED DESCRIPTION OF THE INVENTION

It was an object of the present invention to overcome one or more disadvantages of the prior art by discovering an improved economically viable process, particularly one that can be executed batchwise, for preparing N-ethyldiisopropylamine with good selectivity, yield and space-time yield (STY). It was to be possible to use, as reactant, an amine in the form of crude material, i.e. an amine product which has not had to be subjected to costly and inconvenient purifying distillation beforehand.

Accordingly, a process for preparing N-ethyldiisopropylamine by reacting acetaldehyde with diisopropylamine and hydrogen at elevated temperature and under pressure in the presence of a heterogeneous hydrogenation catalyst, the catalyst being a supported transition metal catalyst comprising Pd and/or Pt as catalytically active metal, has been found, wherein the diisopropylamine used has a purity of 58% to 94% by weight and impurities as follows: 3% to 20% by weight of water, 3% to 20% by weight of isopropanol, 0% to 2% by weight of others.

If the reactant used is a contaminated crude material, it is generally the case that the product of the reaction will also comprise an increased level of components as impurity. One or more of these impurities can then often be removed from the product only with difficulty or with a high yield loss, if at all. However, a high product purity is often required; for instance, N-ethyldiisopropylamine finds use in the synthesis of active pharmaceutical ingredients.

According to the invention, it has been found that, surprisingly, it is possible to use crude diisopropylamine with a water content and isopropanol content that does not lead to significantly more ethanol formation and yield loss compared to the use of purer diisopropylamine in the reaction with acetaldehyde. Thus, according to Le Chatelier's principle, it would be expected that the presence of water in the reaction mixture would lead to a shift in the reaction equilibrium in favor of the enamine, hydrogenation of which subsequently gives the target product (cf. reaction scheme below), as a result of which more acetaldehyde, viewed in relative terms, would be hydrogenated directly to ethanol.

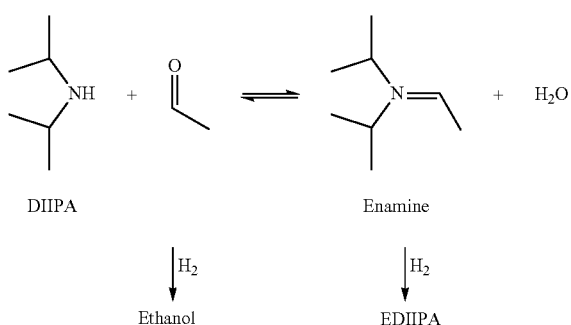

DIIPA    Enamine

Ethanol    EDIIPA

According to the present invention, the conditions and catalyst are chosen such that this relatively high ethanol formation occurs only to a very small degree or particularly not at all. Moreover, it is surprising that, under the conditions of the invention, there is no significant acetal formation resulting from the reaction of isopropanol with acetaldehyde (cf. reaction scheme below). Further yield loss as a result of this acetal formation thus advantageously likewise occurs only to a very small degree or particularly not at all.

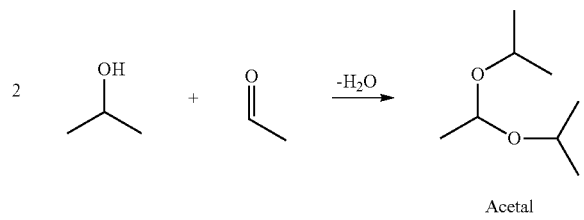

Acetal

In addition, the secondary components derived from isopropanol that form (e.g. N,N-diisopropyl-n-butylamine, N,N-diisopropyl(4-amino-1-butanol)) have very good removability, particularly very good removability by distillation. By means of the process of the invention, even though a crude diisopropylamine is being used, it is nevertheless possible to obtain a very pure end product (N-ethyldiisopropylamine) with high yield, this being suitable as a feedstock, for example, for the synthesis of active pharmaceutical ingredients.

The diisopropylamine used in the process of the invention has a purity of only 58% to 94% by weight and impurities as follows:

3% to 20% by weight of water, 3% to 20% by weight of isopropanol, 0% to 2% by weight of others.

Preferably, the diisopropylamine used in the process of the invention has a purity of only 62.5% to 90% by weight and impurities as follows:

5% to 18% by weight of water, 5% to 18% by weight of isopropanol, 0% to 1.5% by weight of others.

Further preferably, the diisopropylamine used in the process of the invention has a purity of only 69.0% to 85.9% by weight and impurities as follows:

7% to 15% by weight of water, 7% to 15% by weight of isopropanol, 0.1% to 1.0% by weight of others.

(All percentages by weight based on the weight of the crude diisopropylamine used).

The other substances are especially N- and/or O-containing organic compounds, as listed particularly in the working examples cited below.

More preferably, the crude diisopropylamine used was obtained beforehand as a by-product of a reaction of isopropanol with ammonia to give monoisopropylamine (alcohol amination), and, in a further preferred embodiment, the isopropanol used therein was obtained beforehand by a reaction of acetone with hydrogen (hydrogenation).

Such reactions are described in WO 2013/075974 A (BASF SE).

Preference is given to the reaction of isopropanol with ammonia to give monoisopropylamine (MIPA) in the presence of $H_2$ at 20 to 80 bar, 150 to 225° C., a 1.5- to 5-fold molar excess of $NH_3$ based on isopropanol and a Cu-containing heterogeneous catalyst, especially the catalyst disclosed in EP 696 572 A (BASF AG), the catalytically active composition of which, prior to reduction with hydrogen, comprises 20% to 85% by weight of $ZrO_2$, 1% to 30% by weight of oxygen compounds of copper, calculated as CuO, 30% to 70% by weight of oxygen compounds of nickel, calculated as NiO, 0.1% to 5% by weight of oxygen compounds of molybdenum, calculated as $MoO_3$, and 0% to 10% by weight of oxygen compounds of aluminum and/or manganese, calculated respectively as $Al_2O_3$ and $MnO_2$, for example the catalyst which is disclosed in loc. cit., page 8, and has the composition of 31.5% by weight of $ZrO_2$, 50% by weight of NiO, 17% by weight of CuO and 1.5% by weight of $MoO_3$. The catalyst hourly space velocity is, for example, in the range from 0.10 to 0.14 kg of isopropanol/ ($I_{cat.} \cdot h$) ($I_{cat.}$=bed volume).

The reaction mixture obtained as the product of the reaction of isopropanol with ammonia to give monoisopropylamine is worked up, preferably by distillation, particularly by distillation as follows, by 1. removing ammonia ($NH_3$),
2. removing MIPA,
3. removing secondary components having higher boiling points than MIPA and DIIPA,
4. removing ternary isopropanol-DIIPA-water azeotrope.

Preference is given to the reaction of acetone with hydrogen to give isopropanol at 30 to 90 bar, 50 to 160° C., with a 1- to 3-fold molar excess of $H_2$ based on acetone and in the presence of a Cu-containing heterogeneous catalyst, especially an alumina-supported Cu catalyst, for example the shaped copper chromite(III) catalyst described in EP 563 327 A=WO 92/10290 A1 (Engelhard Corp.), prepared from a mixture comprising 20% to 80% by weight of copper chromite(III), in which preferably some or all of the copper chromite(III) has the formula $CuO \cdot CuCr_2O_4$, and 20% to 80% by weight of at least one extrudable inorganic binder material, in which the catalyst has a surface area of 20 to 225 $m^2/g$ and the total pore volume of the pores having a diameter of up to 9500 nanometers (95 000 angströms) in the catalyst is 0.35 to 1 $cm^3/g$.

The supported transition metal catalyst used in the process of the invention is preferably used in the form of a suspension catalyst, in which case the heterogeneous catalyst is thus suspended in a liquid phase of the reaction mixture.

Transition metal catalysts preferred in accordance with the invention are those which comprise, as active components, one or more metals selected from the group of the metals Pd and Pt. Particular preference is given to the metal Pd as at least one and especially the sole active component (active component=catalytically active component).

Support materials for the catalysts for use in accordance with the invention are preferably activated carbon or alumina, more preferably activated carbon.

A catalyst which is particularly preferred in the context of the present invention is Pd on activated carbon (Pd/C).

The catalysts mentioned advantageously have a Pd and/or Pt content of 0.1% to 25% by weight, preferably of 0.5% to 15% by weight and more preferably of 4% to 11% by weight [based in each case on the reduced metal(s) (oxidation state 0) in the finished catalyst and based on the total weight of the dry catalyst].

Catalysts of this kind are commercially available and are obtainable, for example, under the names Degussa E1002, Degussa E101, Degussa E105, Degussa E106, Engelhard C3630, Heraeus K201, Heraeus K202, Heraeus K203, Heraeus K204, Heraeus K219.

The catalyst chosen is advantageously used in such an amount that the amount of catalyst (calculated in anhydrous form) based on the amount of diisopropylamine used is in the range from 0.1% to 20.0% by weight, particularly in the range from 0.5% to 5.0% by weight.

The suspension catalyst may particularly have a water content in the range from 1% to 150% by weight, more particularly in the range from 3% to 10% by weight (based in each case on the weight of the dry catalyst).

In a preferred embodiment, the reaction in the process of the invention is conducted without addition of promoters in the catalyst, for example zinc dopants, or auxiliaries, for example carbon monoxide.

In one embodiment of the invention, the reaction is conducted in the liquid phase or in a mixed liquid/gas phase with at least 50% by weight of the reaction mixture in the liquid phase.

Reactors used may, for example, be stirred tanks, autoclaves, loop reactors or packed bubble columns. A preferred reactor is a stirred tank.

The process of the invention can be conducted continuously or more preferably batchwise, the catalyst preferably being arranged in the form of a suspension catalyst in the reactor.

The process can be conducted in the liquid phase or in the gas phase. Preference is given to an at least partial presence and preferably by far the predominant presence of liquid phase. According to the reaction conditions chosen (pressure, temperature), a certain proportion of the reactants will be in gaseous form in accordance with the partial pressure.

The two reactants, diisopropylamine and acetaldehyde, may be used in a stoichiometric, superstoichiometric or substoichiometric molar ratio. Preference is given to conducting the reaction in the presence of excess acetaldehyde.

The molar ratio of acetaldehyde to diisopropylamine (calculated as 100%) is preferably 1.0 to 5.0 mol/mol, particularly 1.1 to 2.0 mol/mol, more particularly 1.2 to 1.5 mol/mol.

Particular preference is given to a semi-batchwise mode of operation in which the amine and the catalyst are initially charged and then the aldehyde is metered in at reaction temperature and pressure.

The addition is effected continuously or in portions, preferably within 0.5 to 24 hours, further preferably within 1 to 15 hours. The conversion is checked at successive junctures, for example every 30 min or every 15 min, or continuously, for example by online gas chromatography or online spectroscopy. The conversion is monitored, for example, by taking a small sample from the reactor and analyzing the composition, for example by means of gas chromatography. The conversion (C) is calculated from the quotient of the proportions of the products formed from the nitrogen compound used and the sum total of the proportions of the products formed from the nitrogen compound and unconverted nitrogen compound according to the following formula:

$$C = \frac{n_2}{n_2 + n_1} * 100\%$$

with $n_2$=molar amount of products formed from the nitrogen compound and $n_1$=molar amount of unconverted nitrogen compound.

The aldehyde is preferably metered in until a conversion of at least 95%, preferably at least 96%, more preferably at least 97%, e.g. 97.5% to 99.8%, has been attained, based in each case on nitrogen compound used.

In a particularly preferred embodiment of the invention, the rate of addition of the aldehyde is chosen such that the maximum reaction temperature desired in each case (preferably in the range from 70 to 180° C.) is not exceeded (rate of addition, for example, in mol of aldehyde per 30 min).

In the case of addition of aldehyde to the nitrogen compound, reactions in which heat is released proceed: the enamine intermediate is formed in an exothermic reaction with elimination of water. The intermediate is then converted to the product in a further exothermic reaction in the presence of hydrogen and the hydrogenation catalyst (hydrogenation of the double bond). The reaction temperature can be monitored and limited in a very simple manner, by slowing or briefly interrupting the addition of the aldehyde prior to attainment of a maximum temperature fixed beforehand, until the reaction mixture has been lowered again by the emission of heat from the reaction vessel or using an external cooling system.

On conclusion of the reaction, the catalyst is left to settle out in the reaction vessel, forming two phases (an organic phase and an aqueous phase) in the reaction mixture. The organic phase and preferably a portion of the aqueous phase is then run out of the reactor, preferably through a filter.

The reaction temperature can be guided by the activity of the catalyst. The reaction temperature is preferably in the range from 15 to 180° C., preferably 30 to 170° C., more preferably 70 to 160° C., further preferably 100 to 140° C.

The process of the invention is preferably conducted at an absolute pressure (=reaction pressure) in the range from 1 to 120 bar, preferably 5 to 100 bar, more preferably 10 to 80 bar. The pressure in the reactor, which arises from the sum total of the partial pressures of the amine reactant, the acetaldehyde, the impurities and the reaction products formed at the temperatures specified, is appropriately increased to the desired reaction pressure by injecting hydrogen.

Preference is given to operating at an offgas rate of 0.1 to 400 standard cubic meters/(h·(liters of reaction volume)), especially 1 to 20 standard cubic meters/(h·(liters of reaction volume)).

(standard cubic meters=volume under standard conditions (1 bar abs., 20° C.)).

The employment of higher temperatures, higher total pressures and smaller amounts of catalyst is possible.

The workup of the reaction output and isolation of the process product can be effected by the customary methods, for example by fractional continuous or batchwise distillation or rectification. The rectification can be effected, for example, at standard pressure (1 bar abs.) or slightly reduced or elevated pressure, for example at reflux ratios of 1:1 to 10:1 and, for example, in columns having 5 to 60 theoretical plates.

The workup of the reaction output is preferably effected as follows:
1) filtering off the catalyst,
2) phase separation of organic and aqueous phase,
3) removal of the remaining water by distillation,
4) removal of secondary components having lower boiling points than N-ethyldiisopropylamine (EDIIPA) by distillation,
5) removal of secondary components having higher boiling points than EDIIPA by distillation,
6) purifying distillation of EDIIPA.

The distillation yield is generally >80%, particularly >90%.

All pressure figures are based on absolute pressure.

EXAMPLE AND COMPARATIVE EXAMPLE

1) Reaction of crude diisopropylamine (DIIPA) (obtained automatically from a plant for preparation of MIPA) and pure diisopropylamine (DIIPA), each with acetaldehyde over a Pd/C catalyst (5% by weight of Pd on charcoal) to give EDIIPA (Hünig's base)

The crude DIIPA used was obtained automatically in the amination of isopropanol with $NH_3$ to give monoisopropylamine (MIPA) analogously to the process as described in WO 2013/075974 A (BASF SE). For this purpose, isopropanol (0.14 kg/L·h) was reacted with $NH_3$ (molar $NH_3$:iPrOH ratio=2.4) at 46 bar and 196° C. The catalyst used was the catalyst cited in the abovementioned EP application and known from EP 696 572 A (BASF AG), the catalytically active material of which, prior to reduction with hydrogen, has the composition of 31.5% by weight of $ZrO_2$, 50% by weight of NiO, 17% by weight of CuO and 1.5% by weight of $MoO_3$. The reaction mixture was subjected to distillative workup by
1. removing $NH_3$,
2. removing MIPA,
3. removing secondary components having higher boiling points than MIPA and DIIPA,
4. removing ternary isopropanol-DIIPA-water azeotrope.

DIIPA forms a ternary azeotrope with water and isopropanol. Complete removal of isopropanol and water is consequently not achieved by distillation without further measures (breaking of the azeotrope with NaOH or by pressure swing distillation).

This example gave rise to crude DIIPA having a crude DIIPA concentration of 80.0% by weight. Composition of the crude DIIPA (in % by weight):

| | |
|---|---|
| Water | 9.75 |
| Isopropanol | 10.05 |
| Diisopropylamine | 80.0 |
| Others | 0.2 |

The isopropanol used had been obtained beforehand by reacting acetone with hydrogen at 30 to 90 bar, 50 to 160° C., with a 1- to 3-fold molar excess of $H_2$ based on acetone, over an alumina-supported Cu catalyst (29% by weight of CuO, 31% by weight of $Cr_2O_3$, 9% by weight of BaO, 30% by weight of $Al_2O_3$), as described in EP 563 327 A=WO 92/10290 A1 (Engelhard Corp.).

The reaction with acetaldehyde was conducted in semibatchwise mode. DIIPA (as obtained above) or pure DIIPA (comparative) and the Pd/C catalyst (6% by weight in moist form, calculation based on 100% DIIPA) were initially charged in the reaction vessel (0.3 L autoclave) in each case at 120° C. and 25 bar of hydrogen, and acetaldehyde (1.2 molar equivalents based on DIIPA calculated at 100% strength) was metered in within 3 h. Subsequently, stirring was continued at reaction temperature and pressure for 3 h. After cooling and decompression, the phases were separated and analyzed individually by means of GC. After determination of water by means of Karl Fischer titration, the compositions of the organic phases were standardized to 100% by weight. In each case, a synthesis yield of about 80%, based on DIIPA used calculated at 100% strength, was attained. The composition of the crude EDIIPA ex pure DIIPA and crude EDIIPA on crude DIIPA obtained was as follows (in % by weight):

| Component | Crude EDIIPA ex crude DIIPA | Crude EDIIPA ex pure DIIPA |
|---|---|---|
| Ethanol | 0.410 | 0.232 |
| Isopropanol | 5.640 | 0.063 |
| n-Propylamine | 0 | 0.011 |
| n-Butanal | 0.480 | 0.344 |
| n-Butanol | 0.357 | 0.243 |
| DIIPA | 1.274 | 0.205 |
| Enamine | 0 | 0.020 |
| Isopropyl-n-propylamine | 0.004 | 0 |
| 2-Ethylbutanal | 0.362 | 0.288 |
| DEIPA | 0.194 | 0.434 |
| EDIIPA | 82.508 | 93.133 |
| EIPPA | 0.088 | 0.028 |
| DMeBBA | 0.101 | 0.000 |
| DIIP-BA | 6.049 | 4.063 |
| DIIPABol | 1.210 | 0.123 |
| N-Hexyl-DIIPA | 0.343 | 0.192 |
| N-Nonyl-DIIPA | 0.023 | 0.011 |
| Further others | 0.831 | 0.580 |

DEIPA = N,N-Diethylisopropylamine
EIPPA = N-Ethyl-N-isopropyl-n-propylamine
DMeBBA = N-(1,3-Dimethylbutyl)-n-butylamine
DIIP-BA = N,N-Diisopropyl-n-butylamine
DIIPABol = N,N-Diisopropyl(4-amino-1-butanol)

The pure DIIPA used in the comparative experiment had the following composition (in % by weight):

| | |
|---|---|
| Water | 0.01 |
| Isopropanol | 0.00 |
| Diisopropylamine | 99.88 |
| Others | 0.11 |

It can be seen from the examples that the amount of ethanol formed is not significantly more when water is already present at the start of the reaction, and that virtually no acetal (possible reaction of isopropanol with acetaldehyde) and conversion products occur.

The reaction output was worked up as follows in each case:
1) filtering off the catalyst,
2) phase separation of organic phase and aqueous phase,
3) removing remaining water by distillation,
4) removing secondary components having a lower boiling point than N-ethyldiisopropylamine (EDIIPA) by distillation,
5) removing secondary components having a higher boiling point than EDIIPA by distillation,
6) purifying distillation of EDIIPA.

All new secondary components, including the components derived from isopropanol, can easily be removed by distillation. As a result, it was possible, in spite of the crude DIIPA used, to achieve a distillation yield above 80% in the workup.

The composition of the pure EDIIPA obtained ex pure DIIPA on the one hand and ex crude DIIPA on the other hand, which was determined by gas chromatography, was as follows (in % by weight):

| Component | Pure EDIIPA ex crude DIIPA | Pure EDIIPA ex pure DIIPA |
|---|---|---|
| EDIIPA | 99.840 | 99.891 |
| iPrOH | 0.006 | 0.007 |
| DIIPA | 0.016 | 0.009 |
| DEIPA | 0.001 | 0.003 |
| EIPPA | 0.038 | 0.030 |
| Others | 0.099 | 0.061 | iPrOH = isopropanol

The invention claimed is:

1. A process for preparing N-ethyldiisopropylamine comprising reacting acetaldehyde with diisopropylamine and hydrogen in the presence of a heterogeneous hydrogenation catalyst, the catalyst being a supported transition metal catalyst comprising Pd and/or Pt as catalytically active metal, wherein the diisopropylamine is obtained as a by-product of a reaction of isopropanol with ammonia to form monoisopropylamine, the diisopropylamine having a purity of 58% to 94% by weight and impurities that include 3% to 20% by weight of water, and 3% to 20% by weight of isopropanol.

2. The process according to claim 1, wherein the purity of the diisopropylamine is from 62.5% to 90% by weight and the impurities include 5% to 18% by weight of water, and 5% to 18% by weight of isopropanol.

3. The process according to claim 1, wherein the isopropanol is obtained by hydrogenating acetone with hydrogen.

4. The process according to claim 1, wherein product of the reaction of isopropanol with ammonia is subjected to distillative workup that includes successive steps of removing ammonia, removing monoisopropylamine, removing secondary components having higher boiling points than monoisopropylamine and diisopropylamine, and removing ternary isopropanol-diisopropylamine-water azeotrope.

5. The process according to claim 1, wherein the supported transition metal catalyst includes activated carbon as support.

6. The process according to claim 1, wherein the supported transition metal catalyst includes alumina as support.

7. The process according to claim 1, wherein the catalyst has a Pd and/or Pt content in a range from 0.1% to 25% by weight (based on the total weight of the catalyst, without any water present).

8. The process according to claim 1, wherein the catalyst has a Pd and/or Pt content in a range from 0.5% to 15% by weight (based on the total weight of the catalyst, without any water present).

9. The process according to claim 1, wherein the catalyst is in the form of a suspension catalyst.

10. The process according to claim 9, wherein the suspension catalyst is a Pd/C suspension catalyst.

11. The process according to claim 1, wherein the reacting of the acetaldehyde with diisopropylamine is conducted in the presence of excess acetaldehyde.

12. The process according to claim 1, wherein the reacting of the acetaldehyde is conducted at a temperature in a range from 15 to 180° C., and a pressure in a range from 1 to 120 bar.

13. The process according to claim 11, wherein the reacting of the acetaldehyde is conducted at a pressure in the range from 1 to 120 bar.

14. A process for preparing N-ethyldiisopropylamine comprising reacting an excess of acetaldehyde with diisopropylamine and hydrogen at a temperature in a range from 15 to 180° C., and a pressure in a range from 1 to 120 bar, in the presence of a supported transition metal catalyst comprising Pd and/or Pt as catalytically active metal,
wherein the diisopropylamine is obtained as a by-product of a reaction of isopropanol with ammonia to form monoisopropylamine, the diisopropylamine having a purity of 62.5% to 90% by weight and impurities that include 3% to 20% by weight of water, and 3% to 20% by weight of isopropanol.

15. The process according to claim 14, wherein the catalyst is a Pd on activated carbon catalyst.

16. The process according to claim 14, wherein the purity of the diisopropylamine is from 69.0% to 85.9% by weight, and the impurities include 7% to 15% by weight of water, and 7% to 15% by weight of isopropanol.

* * * * *